Figure 1:
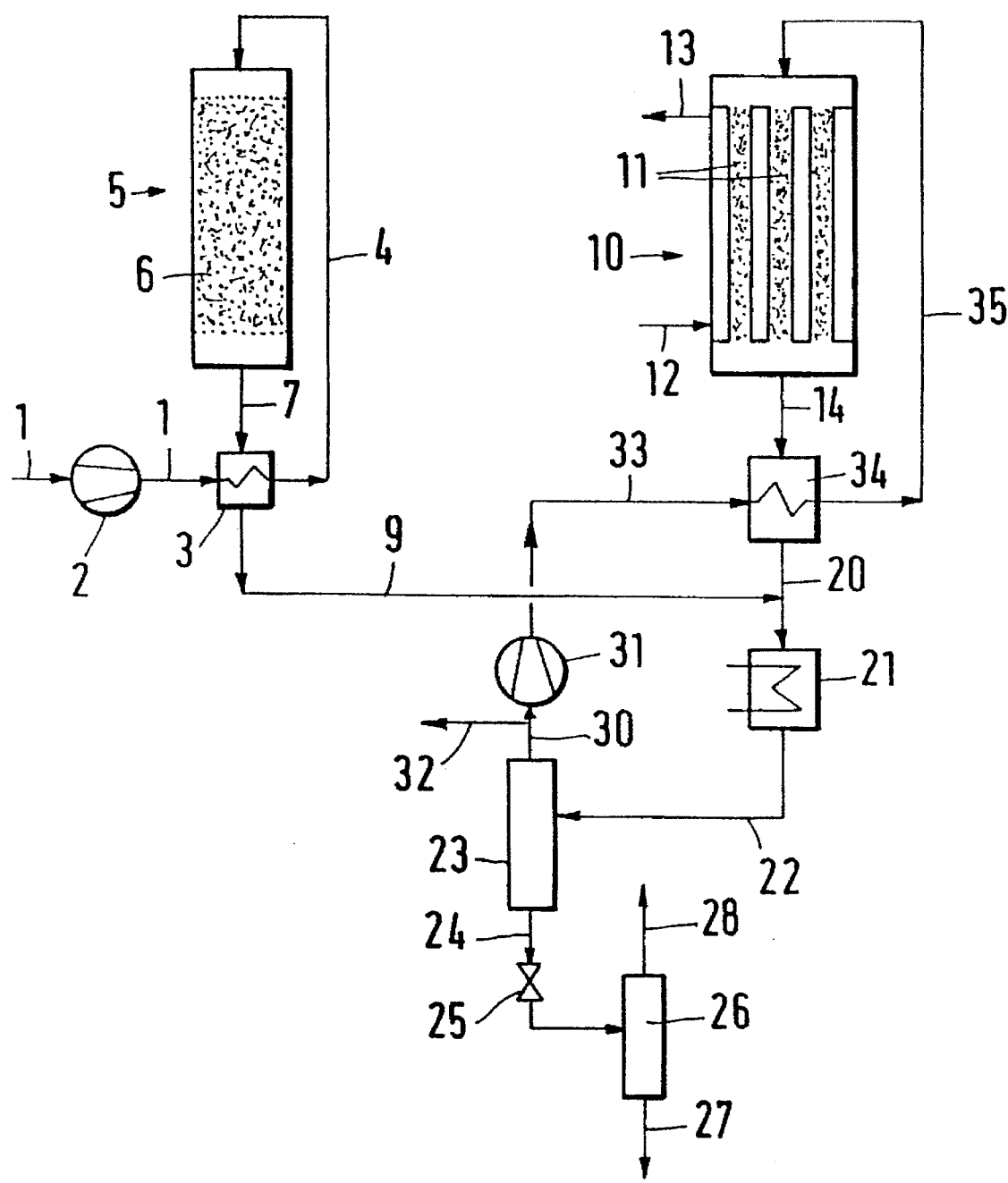

United States Patent [19]

König et al.

[11] Patent Number: 5,631,302
[45] Date of Patent: May 20, 1997

[54] PROCESS OF PRODUCING METHANOL

[75] Inventors: Peter König, Frankfurt am Main; Hermann Göhna, Bad Soden, both of Germany

[73] Assignee: Metallgesellschaft Aktiengesellschaft, Frankfurt am Main, Germany

[21] Appl. No.: 437,255

[22] Filed: May 8, 1995

[30] Foreign Application Priority Data

May 10, 1994 [DE] Germany .................. 44 16 425.4

[51] Int. Cl.$^6$ .................. C07C 27/06; C07C 29/151; C07C 27/26
[52] U.S. Cl. .................. 518/706; 568/913; 518/703; 252/373
[58] Field of Search .................. 518/706, 703; 568/913

[56] References Cited

FOREIGN PATENT DOCUMENTS

| 2705673 | 8/1977 | Germany . | |
|---|---|---|---|
| 3518362 | 11/1986 | Germany . | |
| 102380 | 3/1993 | Romania | 518/706 |
| 528617 | 11/1940 | United Kingdom | 518/706 |
| 1159035 | 7/1969 | United Kingdom | 518/706 |
| 2203427 | 1/1988 | United Kingdom . | |

OTHER PUBLICATIONS

Derwent Abstract, AN 93-186,575, abstract of RO-102382, (1993).
Derwent Abstracts, AN 93-186,574, abstract of RO-102381, (1993).
Ullman's Encyclopedia of Industrial Chemistry, 5th Edition, vol. A16, pp. 467-475—1995.

*Primary Examiner*—Gary L. Geist
*Assistant Examiner*—Sreeni Padmanabhan
*Attorney, Agent, or Firm*—Sprung Horn Kramer & Woods

[57] ABSTRACT

From a synthesis gas which contains hydrogen and carbon oxides, methanol is produced on copper-containing catalysts under pressures in the range from 20 to 20 bars and at temperatures in the range from 200 to 350° C. The synthesis gas is passed through a first synthesis reactor, which consists of a shaft reactor and contains a fixed bed of a copper-containing catalyst. The reaction in the shaft reactor is carried out adiabatically and without a recycling of synthesis gas. Together with recycle gas, the gas mixture which has not been reacted in the first synthesis reactor is passed through a second synthesis reactor, which contains a copper-containing catalyst, which is disposed in tubes and is indirectly cooled through boiling water. 10 to 30% of the carbon oxides of the synthesis gas are reacted in the shaft reactor to form methanol.

7 Claims, 2 Drawing Sheets

PROCESS OF PRODUCING METHANOL

DESCRIPTION

This invention relates to a process of producing methanol from a synthesis gas which contains hydrogen and carbon oxides by a reaction on copper-containing catalysts under pressures in the range from 20 to 120 bars and at temperatures in the range from 200° to 350° C., wherein the synthesis gas is passed through a first synthesis reactor, a first product mixture, which contains methanol vapor, is withdrawn from the first synthesis reactor, the first product mixture is cooled to condense methanol, which is then separated form the gaseous components of the first product mixture, the gaseous components of the first product mixture are fed to a second synthesis reactor, a second product mixture, which contains methanol vapor, is withdrawn from the second synthesis reactor, the second product mixture is cooled to condense methanol, which is separated from the gaseous components of the second product mixture, and at least part of the gaseous components of the first and second product mixtures is fed to the second synthesis reactor.

A process of that kind is described in DE-A-3 518 362. In that process the first and second synthesis reactors which are employed consist each of a shaft reactor, which contains a catalyst bed, which is indirectly cooled by water. As a result, the two reactors are substantially iso-thermally operated. Details of the synthesis of methanol and of the production of the synthesis gas are described in Ullmann's Encyclopedia of Industrial Chemistry, 5th edition, Volume A16, on pages 467 to 475. That disclosure covers the synthesis in a tubular reactor as well as in an adiabatically operated shaft reactor.

It is an object of the invention to effect the synthesis of methanol from a synthesis gas which contains hydrogen and carbon dioxide at low cost with use of a relatively small tubular reactor. In the process described first hereinbefore this is accomplished in accordance with the invention in that the synthesis gas is fed at an inlet temperature in the range from 220° to 270° C. to the first synthesis reactor, which consists of a shaft reactor and contains a fixed bed of a copper-containing catalyst, the reaction in the shaft reactor is carried out adiabatically and without a recycling of synthesis gas, and the second synthesis reactor contains a copper-containing catalyst, which is contained in tubes and is indirectly cooled by boiling water. The first part of the synthesis is carried out in the shaft reactor without a cooling step, which otherwise in known shaft reactors is effected either by an indirect heat exchange with a cooling fluid or in that cold synthesis gas is admixed. It is desirably ensured that 10 to 30% of the carbon oxides which are fed to the shaft reactor, i.e., of the total of CO+$CO_2$, are reacted to form methanol in the shaft reactor.

It is recommendable to feed to the shaft reactor a synthesis gas which has a stoichiometric number $$S=(H_2-CO_2):(CO+CO_2)$$

that amounts to at least 1.9 and which consists mainly of hydrogen and contains 0 to 20% by volume CO and 10 to 25% by volume $CO_2$ while the volume ratio of $CO_2$:CO is at least 1. Particularly the following reactions are significant in the synthesis of methanol:

(1) $CO+2H_2 \rightarrow CH_3OH-90.5$ kJ/mole (2) $CO_2+3H_2 \rightarrow CH_3OH+H_2O-49.4$ kJ/mole (3) $CO_2+H_2 \rightarrow CO+H_2O+41.1$ kJ/mole If the synthesis gas has a relatively low CO content but a relatively high content of $CO_2$, the synthesis in the adiabatically operated shaft reactor will not result between the inlet and outlet in a temperature rise or will result there only in a small temperature rise. For this reason the temperatures in the shaft reactor may be maintained in the range from 220° to about 300° C., as is favorable for the copper catalysts.

In the process in accordance with the invention a major part of the methanol, usually 70 to 90% of the total amount produced in the shaft reactor and the tubular reactor, is produced in the tubular reactor on the indirectly cooled catalyst. This means, on the one hand, that the expensive tubular reactor may be much smaller so that it requires a lower apparatus expenditure than a tubular reactor in which the entire amount of methanol would be produced. In known manner, boiling water is used as a coolant in the tubular reactor so that steam is formed, which is additionally valuable because it becomes available under a high pressure. Another important aspect of the process in accordance with the invention resides in that the rate at which high-pressure steam is produced in the tubular reactor is hardly lower than in a single-stage process without a preceding shaft reactor. In the process in accordance with the invention steam is produced in the tubular reactor at a relatively high rate because that heat is released only at a low rate in the receding shaft reactor and by far the major part of the surplus exothermic energy becomes effective only in the tubular reactor.

To optimally achieve the above-mentioned advantages to the highest possible degree and to minimize the capital investment required for a production plant, care must be taken, inter alia, that the shaft reactor must be as simple in construction as possible. In order to eliminate the need for means for cooling that unit, the above-mentioned criteria for the synthesis gas must be met and pressure-dependent changes of the reaction intensities must be taken into account in that connection. The synthesis gas fed to the shaft reactor has desirably a CO content of 0 to 15% by volume and may contain 15 to 25% by volume $CO_2$. The volume ratio of $CO_2$:CO desirably exceeds 2:1 and the CO content is in most cases not in excess of 10% by volume. The synthesis gas fed to the shaft reactor may alternately be entirely free of carbon monoxide.

The pressures in the shaft reactor and in the tubular reactor in a methanol synthesis plant may generally be determined in either of two ways. In one case approximately the same pressure is maintained in both reactors so that succeeding parts of the plant may be used in common. In the other case the shaft reactor and the tubular reactor are operated under greatly different pressures.

If approximately the same pressure is selected for both reactors and a pressure difference not in excess of 5 bars is called for, it will be desirable to operate both reactors under pressures in the range from 60 to 100 bars, preferably in the range from 70 to 90 bars. On the other hand, if a higher pressure difference between the shaft reactor and the tubular reactor is permissible, it will be recommendable to operate the shaft reactor under a pressure in the range from 20 to 60 bars and the tubular reactor under a pressure in the range from 50 to 100 bars. In the latter case the pressure in the shaft reactor may be lower than the pressure in the tubular reactor by at least 7 bars in most cases.

In the process in accordance with the invention wherein the $CO_2$ content of the synthesis gas is relatively high and the CO content of the synthesis gas is relatively low, it is recommendable to use Cu—Zn catalysts having an atomic ratio Cu/Zn from 2:1 to 4:1. In general the catalyst comprises 50 to 75% by weight CuO, 15 to 35% by weight ZnO, and 5 to 20% by weight $Al_2O_3$.

Besides, the desirable catalysts have a BET surface area of at least 100 m²/g and, in combination therewith a specific pore structure. Hereinafter, pores which are 2.0 to 7.5 nm in diameter will be described as mesopores and pores which are more than 7.5 nm in diameter as macropores. Numerically, the proportion of mesopores in the catalyst is in the range from 20 to 40% and the proportion of macropores in the range from 80 to 60%. The numerical proportion of the pores which are less than 2 nm in diameter is not in excess of 1%.

A catalyst of the preferred type may be prepared, e.g., as follows:

A first solution is prepared from 418 g copper nitrate, 50 g zinc oxide, 1.6 liter water and 128 g $HNO_3$ (52.5%). A colloidal aluminum metahydrate gel is added to that solution. To prepare that gel 30 g of the 52.5% nitric acid are added to an AlO(OH) sol at 50° C. with slow stirring to peptize the particles of aluminum metahydrate. A second solution comprises 410 g sodium carbonate dissolved in 2 liters water. The two solutions are separately heated to 68° C. and are combined with strong stirring in such a manner that the pH amounts to 6.7 during the precipitation. The precipitate is aged at 68° C. with stirring for one hour in the mother liquor and is subsequently filtered off and dried at 120° C. and thereafter calcined at 280° C. for 8 hours. The calcined product is reduced in size and after an addition of 2% by weight graphite is compressed to form tablets. The resulting catalyst precursor comprises 67.4% CuO, 21.4% by weight ZnO, and 11.1% by weight $Al_2O_3$. The pore volume measured by mercury porosimetry is 0.34 ml/g. The pores consist of 42% mesopores and 58% macropores.

Further features of the process will be explained with reference to the drawing, in which FIG. 1 illustrates a first mode of carrying out the process and FIG. 2 a second mode of the process.

In the mode illustrated in FIG. 1 the synthesis gas supplied through line 1 and conveyed by the compressor 2 is heated to temperatures in the range from 220° to 270° C. in the heat exchanger 3 and through line 4 is fed to the shaft reactor 5. The shaft reactor contains a fixed bed 6 of a granular copper catalyst. The reaction in the shaft reactor 5 is carried out without a cooling and without a recycling of synthesis gas only in that the fresh synthesis gas is passed a single time through the reactor. A first product mixture, which contains methanol vapor, is withdrawn from the bottom end of the reactor 5 through line 7. 10 to 30% of the carbon oxides (CO+CO₂) of the synthesis gas in line 4 are usually reacted to form methanol in the shaft reactor.

A first cooling of the product mixture is effected in the heat exchanger 3. The product mixture then flows in line 9 and is combined in line 20 with the second product mixture, which comes from the tubular reactor 10. In the cooler 21 the two product mixtures are cooled sufficiently to condense methanol. Thereafter the mixture flows through a line 22 to a separator 23. High-methanol condensate is withdrawn through line 24 and is conducted through an expansion valve 25 to a second separator 26. Raw methanol becomes available in line 27 and residual gas leaves the separator 25 through line 28. The raw methanol in line 27 is fed to a known distilling purification, which is not shown.

The recycle gas withdrawn from the top of the separator 23 is conducted in part through a line 30 to a compressor 31 and a part of the gas is removed from the process through line 32 in order to limit the content of inert gases. Containing the components $H_2$, CO, and $CO_2$ of the synthesis gas the recycle gas is first conducted in line 33 to the heat exchanger 34 and is heated therein to temperatures of about 200° to 250° C. and is subsequently fed in line 35 to the tubular reactor 10. The tubular reactor 10 is provided in known manner with a large number of tubes 11, which contain a granular copper catalyst. The catalyst is indirectly cooled by water which is boiling under a high pressure and is fed in line 12. The resulting steam is withdrawn in line 13. Because that steam becomes available under a pressure which corresponds to the temperature prevailing in the tubes 11 as a boiling temperature, that steam is highly valuable for its further use.

The product mixture which has been produced in the tubular reactor 10 flows through line 14 to the heat exchanger 34, in which a first cooling is effected, and the product mixture is subsequently combined in line 20 with the product mixture which is supplied from line 9.

In the process of FIG. 1 the pressure in the shaft reactor 6 and in the tubes 11 of the tubular reactor 10 is approximately the same and the pressure selected in the shaft reactor 6 is preferably higher by 1 to 5 bars so that the product mixture produced therein readily flows through lines 7 and 9 to the line 20. The pressures in the two reactors 6 and 10 are in the range from 20 to 120 bars and are preferably at least 40 bars.

Figure 2:
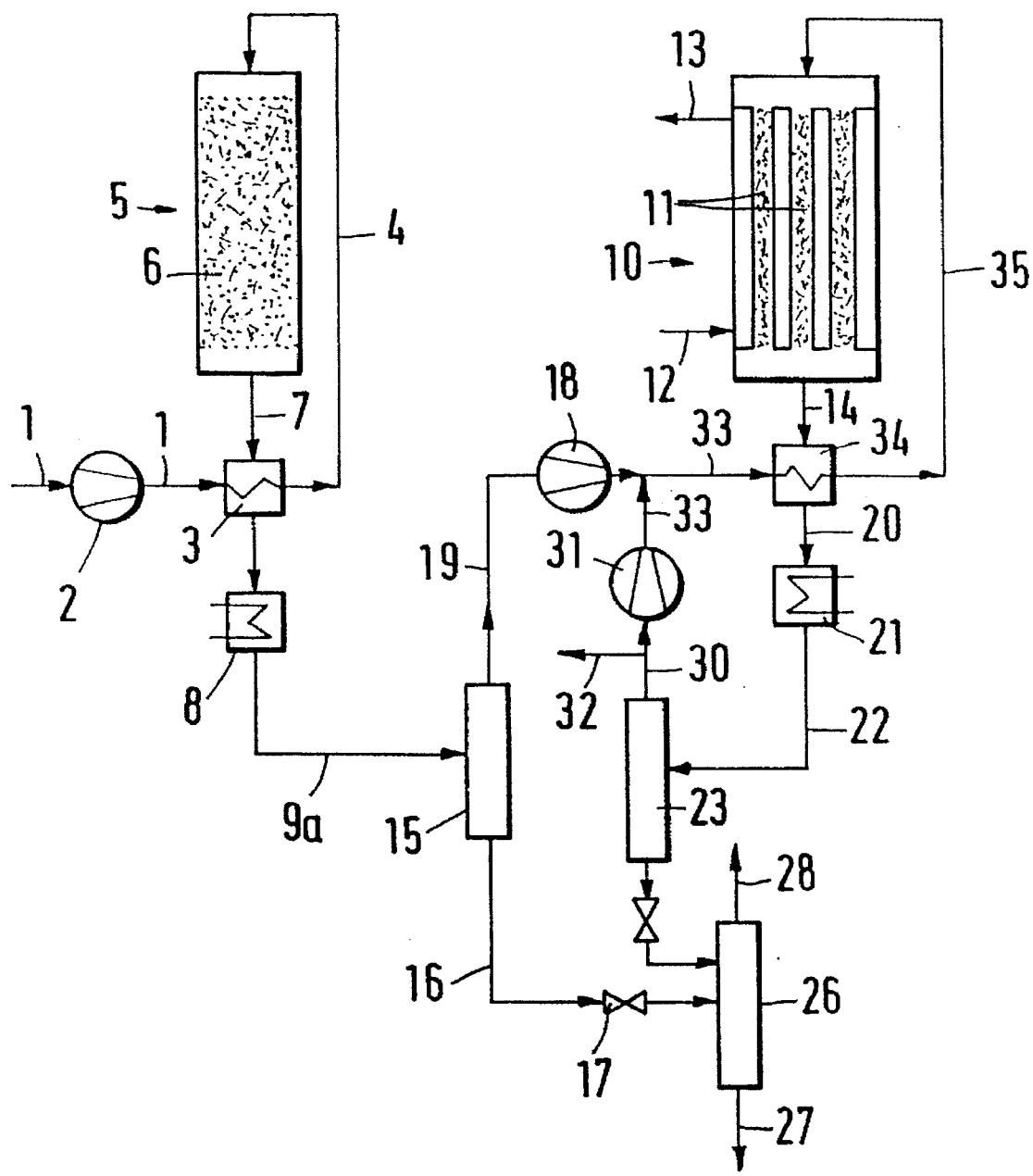

In the process of FIG. 2 the shaft reactor 6 and the tubular reactor 10 are operated under pressures which differ considerably and in most cases the pressure in the shaft reactor is at least 7 bars lower than the pressure in the tubular reactor. Preferably the pressure in the shaft reactor 6 is 20 to 60 bars and the pressure in the tubes 11 of the tubular reactor 10 is 50 to 100 bars. Owing to that pressure difference the first product mixture coming from the heat exchanger 3 is conducted through a cooler 8, in which methanol is condensed, and the mixture is subsequently conducted through line 9a to a separate separator 15. High-methanol condensate from the separator 15 is first conducted through line 16 to an expansion valve 17 and is then fed to the separator 26. Residual gas which contains the components $H_2$, CO and $CO_2$ of the synthesis gas is withdrawn in line 19 from the separator 15 by means of the compressor 18 and is supplied to the line 33, in which the recycle gas is conducted, which in the manner described with reference to FIG. 1 is conducted in line 35 to the tubular reactor 10. In its further details the mode of the process illustrated in FIG. 2 agrees with that explained with reference to to FIG. 1 and plant parts having the same reference numerals have the functions which have been explained hereinbefore.

EXAMPLE 1

In a process as illustrated in FIG. 1, a synthesis gas having the composition stated in column A of Table I is conducted in line 1.

TABLE I

|  | A | B |
| --- | --- | --- |
| $CO_2$ | 23.9 (mole %) | 22.1 (mole %) |
| CO | 0.3 (mole %) | 2.2 (mole %) |
| $H_2$ | 73.9 (mole %) | 73.8 (mole %) |
| $CH_4$ | 1.2 (mole %) | 1.2 (mole %) |
| $N_2$ | 0.7 (mole %) | 0.7 (mole %) |

The same catalyst is used in the shaft reactor 5 and the tubular reactor 10 and comprises 67.4% by weight CuO, 21.4% by weight ZnO, and 11.1% by weight $Al_2O_3$ and before the beginning of the synthesis is reduced in conventional manner. The shaft reactor contains 200 kg catalyst and the tubular reactor contains 800 kg catalyst. The shaft reactor is operated under a pressure of 80 bars and the pressure in the tubes of the tubular reactor is about 78 bars. Synthesis gas at a rate of 11000 sm$^3$ (sm$^3$=standard cubic meter) per hour and per m$^3$ catalyst is supplied to the shaft reactor.

The temperatures stated in line T1 of the following Table II prevail in various lines.

TABLE II

| Line | 4 | 7 | 13 | 35 |
|---|---|---|---|---|
| T1 (°C.) | 250 | 286 | 260 | 240 |
| T2 (°C.) | 250 | 279 | 260 | 240 |

The gas-vapor mixture in line 7 has the composition stated in column A of Table III.

TABLE III

| | | A | B | C | D | E |
|---|---|---|---|---|---|---|
| $CO_2$ | (mole %) | 18.5 | 14.0 | 11.3 | 19.8 | 9.8 |
| CO | (mole %) | 3.6 | 3.0 | 2.5 | 5.0 | 2.4 |
| $H_2$ | (mole %) | 64.5 | 69.1 | 62.0 | 72.9 | 71.1 |
| $CH_4$ | (mole %) | 1.3 | 8.4 | 9.3 | 1.4 | 10.2 |
| $N_2$ | (mole %) | 0.8 | 5.1 | 5.6 | 0.8 | 6.3 |
| $CH_3OH$ | (mole %) | 4.0 | 0.3 | 5.2 | 0.1 | 0.2 |
| $H_2O$ | (mole %) | 7.3 | 0.1 | 4.1 | — | — |

The tubular reactor is fad through line 35 with a gas-vapor mixture at a rate of 12000 sm$^3$/m$^3$/h, which has the composition stated in column B of Table III. The temperature maximum in the tubes of the reactor 10 is about 270° C. The cooling results in the formation of steam of 48 bars. The gas-vapor mixture which is withdrawn from the tubular reactor in line 14 has the composition stated in column C of Table III. A water-containing product mixture which contains 63.9% by weight methanol becomes available in line 27. For the production of 1000 kg of that product mixture, 142 kilomoles synthesis gas having the composition stated in column A of Table I are supplied through line 1.

EXAMPLE 2

In the process illustrated in FIG. 2 the same catalyst is used in the same amounts in the two reactors 5 and 10 as in Example 1. The composition of the synthesis gas in line 1 has been stated hereinbefore in column B of Table I.

The temperatures in various lines are apparent from line T2 of Table II. Just as in Example 1, synthesis gas at a rate of 11000 sm$^3$/m$^3$/h is fed to the shaft reactor 5. The reactor 5 is operated under a pressure of 60 bars.

A residual gas at a rate of 0.87 kilomole per kilomole synthesis gas in line 1 is withdrawn through line 19 and together with the gas conducted in line 33 is compressed to 100 bars and at that pressure enters the tubular reactor 10. The composition of the residual gas in line 19 is apparent from column D of Table III and column E relates to the gas in line 35. The ratio of the rates of the gas streams passing through the compressor 18 and the recycling compressor 31 is 1:4. The product mixture in line 27 comprises 65.8% by weight methanol, balance water. For the production of 1000 kg of that product mixture, 135 kilomoles synthesis gas having the composition stated in column B of Table I are required.

We claim:

1. A process of producing methanol from a synthesis gas containing hydrogen and carbon oxides by reactions in the presence of copper-containing catalysts under pressures in the range from 20 to 120 bars and at temperatures in the range from 200° to 350° C., wherein the synthesis gas is fed into a first synthesis reactor at an inlet temperature in the range from 220° to 270° C., said synthesis gas mainly comprising hydrogen and containing 0 to 15% by volume carbon monoxide and 15 to 25% by volume carbon dioxide, the stoichiometric number S=$(H_2-CO_2):(CO+CO_2)$ of said synthesis gas being at least 1.9 and the volume ratio $CO_2:CO$ of said synthesis gas being at least 2:1, said first synthesis reactor being a single shaft reactor containing a fixed bed of a copper-containing catalyst, reaction in said shaft reactor being carried out adiabatically and without a recycling of synthesis gas, furthermore, there being no indirect cooling of said fixed bed of catalyst and no synthesis gas being fed into said fixed bed for cooling purposes, from the first synthesis reactor withdrawing a first product mixture containing methanol vapor, cooling said first product mixture and condensing methanol, separating condensed methanol from the gaseous components of the first product mixture and feeding the gaseous components to an inlet of a second synthesis reactor, said second synthesis reactor containing tubes which are indirectly cooled by boiling water, said tubes containing a copper-containing catalyst and said gaseous components are passed through said tubes, a second product mixture containing methanol vapor is withdrawn from an outlet of said second synthesis reactor, said second product mixture being cooled to condense methanol, separating condensed methanol from the gaseous components of the second product mixture and feeding at least part of the gaseous components of the first and second product mixtures to the inlet of said second synthesis reactor.

2. A process according to claim 1, characterized in that 10 to 30% of the carbon oxides are reacted in the shaft reactor to form methanol.

3. A process according to claims 1, characterized in that the pressures in the shaft reactor and in the tubular reactor are in the range from 60 to 100 bars and the pressures in the two reactors differ by less than 5 bars.

4. A process according to claim 3, characterized in that the pressures in the shaft reactor and in the tubular reactor are in the range from 70 to 90 bars.

5. A process according to claim 1, characterized in that a pressure in the range from 20 to 60 bars prevails in the shaft reactor, a pressure in the range from 50 to 100 bars prevails in the tubular reactor and the pressure in the shaft reactor is at least 7 bars lower than the pressure in the tubular reactor.

6. A process according to claim 1, characterized in that a catalyst comprising 50 to 75% by weight CuO, 15 to 35% by weight ZnO, and 5 to 20% by weight $Al_2O_3$ is used in the shaft reactor and in the tubular reactor.

7. A process according to claim 6, characterized in that the catalyst has a Cu:Zn atomic ratio of from 2:1 to 4:1.

* * * * *